(12) United States Patent
Drasler et al.

(10) Patent No.: US 7,416,557 B2
(45) Date of Patent: Aug. 26, 2008

(54) VENOUS VALVE APPARATUS AND METHOD

(75) Inventors: William J. Drasler, Minnetonka, MN (US); Mark L. Jenson, Greenfield, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 664 days.

(21) Appl. No.: 10/692,401

(22) Filed: Oct. 23, 2003

(65) Prior Publication Data

US 2004/0215339 A1 Oct. 28, 2004

Related U.S. Application Data

(60) Provisional application No. 60/420,905, filed on Oct. 24, 2002.

(51) Int. Cl.
*A61F 2/06* (2006.01)
(52) U.S. Cl. .................................. 623/1.11; 623/1.24
(58) Field of Classification Search ............... 623/1.16, 623/1.24, 3.1, 1.11; 604/101.05, 101.01
See application file for complete search history.

(56) References Cited

U.S. PATENT DOCUMENTS

| 5,358,518 | A | | 10/1994 | Camilli ........................... 623/2 |
| 5,468,239 | A | * | 11/1995 | Tanner et al. .................. 606/15 |
| 5,820,595 | A | * | 10/1998 | Parodi .................... 604/101.05 |
| 6,241,763 | B1 | * | 6/2001 | Drasler et al. ............... 623/1.24 |
| 6,299,637 | B1 | | 10/2001 | Shaolian et al. ............ 623/1.24 |
| 6,315,793 | B1 | | 11/2001 | Bokros et al. .............. 623/1.24 |
| 6,440,164 | B1 | | 8/2002 | DiMatteo .................... 623/1.24 |
| 6,666,885 | B2 | | 12/2003 | Moe .......................... 623/2.12 |
| 6,666,886 | B1 | | 12/2003 | Tranquillo et al. .......... 623/2.42 |
| 6,669,725 | B2 | | 12/2003 | Scott ........................... 623/2.36 |
| 6,673,109 | B2 | | 1/2004 | Cox ............................ 623/2.12 |
| 6,676,698 | B2 | | 1/2004 | McGuckin, Jr. et al. ..... 623/1.24 |
| 6,676,702 | B2 | | 1/2004 | Mathis ....................... 623/2.36 |
| 6,682,558 | B2 | | 1/2004 | Tu et al. ..................... 623/2.11 |

(Continued)

FOREIGN PATENT DOCUMENTS

WO          WO 88/00459          1/1988

(Continued)

OTHER PUBLICATIONS

International Search Report, Mar. 24, 2004 (4 pgs.).

(Continued)

*Primary Examiner*—Thomas J Sweet
*Assistant Examiner*—Jonathan R Stroud
(74) *Attorney, Agent, or Firm*—Brooks, Cameron & Huebsch, PLLC

(57) ABSTRACT

Embodiments of the invention provide for a unidirectional flow valve. For example, embodiments of the invention include a method of providing a unidirectional flow valve to a vein that include folding a first portion of a vein over an adjacent second portion of a vein and engaging at least two opposing areas of the second portion of the vein to adjacent areas of the first portion of the vein. The at least two opposing walls of the second portion of the vein define the unidirectional flow valve. At least one support device may be inserted into the folded valve region of the vein to maintain the folded configuration of the valve.

6 Claims, 9 Drawing Sheets

U.S. PATENT DOCUMENTS

| | | | |
|---|---|---|---|
| 6,682,559 B2 | 1/2004 | Myers et al. | 623/2.13 |
| 6,685,739 B2 | 2/2004 | DiMatteo et al. | 623/1.24 |
| 6,692,512 B2 | 2/2004 | Jang | 606/200 |
| 6,695,878 B2 | 2/2004 | McGuckin, Jr. et al. | 623/1.19 |
| 6,695,886 B1 | 2/2004 | Kuehn et al. | 606/213 |
| 6,709,456 B2 | 3/2004 | Langberg et al. | 623/2.37 |
| 6,709,457 B1 | 3/2004 | Otte et al. | 623/2.4 |
| 6,716,241 B2 | 4/2004 | Wilder et al. | 623/1.24 |
| 6,716,244 B2 | 4/2004 | Klaco | 623/2.4 |
| 6,719,767 B1 | 4/2004 | Kimblad | 606/151 |
| 6,719,784 B2 | 4/2004 | Henderson | 623/1.44 |
| 6,719,786 B2 | 4/2004 | Ryan et al. | 623/2.11 |
| 6,719,787 B2 | 4/2004 | Cox | 623/2.12 |
| 6,719,788 B2 | 4/2004 | Cox | 623/2.12 |
| 6,719,789 B2 | 4/2004 | Cox | 623/2.13 |
| 6,719,790 B2 | 4/2004 | Brendzel et al. | 623/2.4 |
| 6,723,038 B1 | 4/2004 | Schroeder et al. | 600/16 |
| 6,723,122 B2 | 4/2004 | Yang et al. | 623/2.1 |
| 6,723,123 B1 | 4/2004 | Kazatchkov et al. | 623/2.2 |
| 6,726,715 B2 | 4/2004 | Sutherland | 623/2.1 |
| 6,726,716 B2 | 4/2004 | Marquez | 623/2.36 |
| 6,726,717 B2 | 4/2004 | Alfieri et al. | 623/2.36 |
| 6,730,118 B2 | 5/2004 | Spenser et al. | 623/1.24 |
| 6,730,121 B2 | 5/2004 | Ortiz et al. | 623/2.17 |
| 6,730,122 B1 | 5/2004 | Pan et al. | 623/2.33 |
| 6,736,845 B2 | 5/2004 | Marquez et al. | 623/2.11 |
| 6,736,846 B2 | 5/2004 | Cox | 623/2.12 |
| 6,749,630 B2 | 6/2004 | McCarthy et al. | 623/2.36 |
| 6,752,813 B2 | 6/2004 | Goldfarb et al. | 606/139 |
| 6,752,828 B2 | 6/2004 | Thornton | 623/1.24 |
| 6,755,857 B2 | 6/2004 | Peterson et al. | 623/2.17 |
| 6,761,734 B2 | 7/2004 | Suhr | 623/1.35 |
| 6,761,735 B2 | 7/2004 | Eberhardt et al. | 623/2.1 |
| 6,764,494 B2 | 7/2004 | Menz et al. | 606/159 |
| 6,764,508 B1 | 7/2004 | Roehe et al. | 623/2.11 |
| 6,764,509 B2 | 7/2004 | Chinn et al. | 623/2.12 |
| 6,764,510 B2 | 7/2004 | Vidlund et al. | 623/2.34 |
| 6,767,362 B2 | 7/2004 | Schreck | 623/2.11 |
| 6,769,434 B2 | 8/2004 | Liddicoat et al. | 128/898 |
| 6,770,083 B2 | 8/2004 | Seguin | 606/142 |
| 6,780,200 B2 | 8/2004 | Jansen | 623/2.17 |
| 6,786,924 B2 | 9/2004 | Ryan et al. | 623/2.36 |
| 6,786,925 B1 | 9/2004 | Schoon et al. | 623/2.38 |
| 6,790,229 B1 | 9/2004 | Berreklouw | 623/2.1 |
| 6,790,230 B2 | 9/2004 | Beyersdorf et al. | 623/2.18 |
| 6,790,231 B2 | 9/2004 | Liddicoat et al. | 623/2.37 |
| 6,793,673 B2 | 9/2004 | Kowalsky et al. | 623/2.36 |
| 6,797,000 B2 | 9/2004 | Simpson et al. | 623/2.15 |
| 6,797,001 B2 | 9/2004 | Mathis et al. | 623/2.37 |
| 6,797,002 B2 | 9/2004 | Spence et al. | 623/2.38 |
| 6,802,860 B2 | 10/2004 | Cosgrove et al. | 623/2.11 |
| 6,805,710 B2 | 10/2004 | Bolling et al. | 623/2.36 |
| 6,805,711 B2 | 10/2004 | Quijano et al. | 623/2.37 |
| 6,810,882 B2 | 11/2004 | Langberg et al. | 128/898 |
| 6,821,297 B2 | 11/2004 | Snyders | 623/2.18 |
| 6,824,562 B2 | 11/2004 | Mathis et al. | 623/2.36 |
| 6,830,584 B1 | 12/2004 | Seguin | 623/2.11 |
| 6,830,585 B1 | 12/2004 | Artof et al. | 623/2.11 |
| 6,837,902 B2 | 1/2005 | Nguyen et al. | 623/2.13 |
| 6,840,246 B2 | 1/2005 | Downing | 128/898 |
| 6,840,957 B2 | 1/2005 | DiMatteo et al. | 623/1.24 |
| 6,846,324 B2 | 1/2005 | Stobie | 623/2.17 |
| 6,846,325 B2 | 1/2005 | Liddicoat | 623/2.4 |
| 6,858,039 B2 | 2/2005 | McCarthy | 623/2.36 |
| 6,869,444 B2 | 3/2005 | Gabbay | 623/2.36 |
| 6,872,226 B2 | 3/2005 | Cali et al. | 623/2.13 |
| 6,875,224 B2 | 4/2005 | Grimes | 606/219 |
| 6,875,230 B1 | 4/2005 | Morita et al. | 623/2.12 |
| 6,875,231 B2 | 4/2005 | Anduiza et al. | 623/2.14 |
| 6,881,199 B2 | 4/2005 | Wilk et al. | 604/9 |
| 6,881,224 B2 | 4/2005 | Kruse et al. | 623/2.11 |
| 6,883,522 B2 | 4/2005 | Spence et al. | 128/898 |
| 6,890,352 B1 | 5/2005 | Lentell | 623/2.27 |
| 6,890,353 B2 | 5/2005 | Cohn et al. | 623/2.37 |
| 6,893,459 B1 | 5/2005 | Macoviak | 623/2.11 |
| 6,893,460 B2 | 5/2005 | Spenser et al. | 623/2.14 |
| 6,896,700 B2 | 5/2005 | Lu et al. | 623/2.34 |
| 6,902,576 B2 | 6/2005 | Drasler et al. | 623/1.24 |
| 6,908,478 B2 | 6/2005 | Alferness et al. | 623/1.11 |
| 6,908,481 B2 | 6/2005 | Cribier | 623/2.11 |
| 6,911,043 B2 | 6/2005 | Myers et al. | 623/2.13 |
| 6,913,608 B2 | 7/2005 | Liddicoat et al. | 606/151 |
| 6,916,338 B2 | 7/2005 | Speziali | 623/2.12 |
| 6,918,917 B1 | 7/2005 | Nguyen et al. | 606/139 |
| 6,921,407 B2 | 7/2005 | Nguyen et al. | 606/142 |
| 6,921,811 B2 | 7/2005 | Zamora et al. | 536/21 |
| 6,926,715 B1 | 8/2005 | Hauck et al. | 606/41 |
| 6,926,730 B1 | 8/2005 | Nguyen et al. | 606/213 |
| 6,929,653 B2 | 8/2005 | Strecter | 606/200 |
| 6,932,838 B2 | 8/2005 | Schwartz et al. | 623/1.23 |
| 6,936,067 B2 | 8/2005 | Buchanan | 623/2.28 |
| 6,939,359 B2 | 9/2005 | Tu et al. | 606/159 |
| 6,942,694 B2 | 9/2005 | Liddicoat et al. | 623/2.36 |
| 6,945,957 B2 | 9/2005 | Freyman | 604/96.01 |
| 6,945,978 B1 | 9/2005 | Hyde | 606/142 |
| 6,945,996 B2 | 9/2005 | Sedransk | 623/2.12 |
| 6,945,997 B2 | 9/2005 | Huynh et al. | 623/2.17 |
| 6,949,122 B2 | 9/2005 | Adams et al. | 623/2.36 |
| 6,951,571 B1 | 10/2005 | Srivastava | 623/1.24 |
| 6,951,573 B1 | 10/2005 | Dilling | 623/2.2 |
| 6,953,332 B1 | 10/2005 | Kurk et al. | 425/275 |
| 6,955,689 B2 | 10/2005 | Ryan et al. | 623/2.36 |
| 6,958,076 B2 | 10/2005 | Acosta et al. | 623/1.24 |
| 6,962,605 B2 | 11/2005 | Cosgrove et al. | 623/2.36 |
| 6,964,682 B2 | 11/2005 | Nguyen-Thien-Nhon et al. | 623/2.11 |
| 6,964,683 B2 | 11/2005 | Kowalsky et al. | 623/2.36 |
| 6,964,684 B2 | 11/2005 | Ortiz et al. | 623/2.37 |
| 6,966,925 B2 | 11/2005 | Stobie | 623/2.11 |
| 6,966,926 B2 | 11/2005 | Mathis | 623/2.36 |
| 6,974,464 B2 | 12/2005 | Quijano et al. | 606/108 |
| 6,974,474 B2 | 12/2005 | Pavcnik et al. | 623/1.24 |
| 6,974,476 B2 | 12/2005 | McGuckin, Jr. et al. | 623/2.36 |
| 6,976,995 B2 | 12/2005 | Mathis et al. | 623/2.37 |
| 6,979,350 B2 | 12/2005 | Moll et al. | 623/1.24 |
| 6,986,775 B2 | 1/2006 | Morales et al. | 606/139 |
| 6,989,027 B2 | 1/2006 | Allen et al. | 623/2.18 |
| 6,989,028 B2 | 1/2006 | Lashinski et al. | 623/2.37 |
| 6,997,950 B2 | 2/2006 | Chawla | 623/2.1 |
| 6,997,951 B2 | 2/2006 | Solem et al. | 623/2.37 |
| 7,004,176 B2 | 2/2006 | Lau | 128/898 |
| 7,007,396 B2 | 3/2006 | Rudko et al. | 33/512 |
| 7,011,669 B2 | 3/2006 | Kimblad | 606/151 |
| 7,011,681 B2 | 3/2006 | Vesely | 623/2.11 |
| 7,011,682 B2 | 3/2006 | Lahsinski et al. | 623/2.37 |
| 7,018,406 B2 | 3/2006 | Seguin et al. | 623/2.1 |
| 7,018,407 B1 | 3/2006 | Wright et al. | 623/2.11 |
| 7,018,408 B2 | 3/2006 | Bailey et al. | 623/2.11 |
| 7,022,134 B1 | 4/2006 | Quijano et al. | 623/1.24 |
| 7,025,780 B2 | 4/2006 | Gabbay | 623/2.13 |
| 7,033,390 B2 | 4/2006 | Johnson et al. | 623/2.11 |
| 7,037,333 B2 | 5/2006 | Myers et al. | 623/2.13 |
| 7,037,334 B1 | 5/2006 | Hlavka et al. | 623/2.36 |
| 7,041,128 B2 | 5/2006 | McGuckin, Jr. et al. | 623/1.36 |
| 7,041,132 B2 | 5/2006 | Quijano et al. | 623/2.11 |
| 7,044,966 B2 | 5/2006 | Svanidze et al. | 623/2.1 |
| 7,044,967 B1 | 5/2006 | Solem et al. | 623/2.36 |
| 7,048,754 B2 | 5/2006 | Martin et al. | 606/232 |
| 7,048,757 B2 | 5/2006 | Shaknovich | 623/1.24 |
| 7,052,487 B2 | 5/2006 | Cohn et al. | 604/509 |
| 7,052,507 B2 | 5/2006 | Wakuda et al. | 606/194 |
| 7,063,722 B2 | 6/2006 | Marquez | 623/2.36 |
| 7,066,954 B2 | 6/2006 | Ryan et al. | 623/2.36 |
| 7,070,616 B2 | 7/2006 | Majercak et al. | 623/1.24 |

| | | | | | | |
|---|---|---|---|---|---|---|
| 7,070,618 B2 | 7/2006 | Streeter ............... 623/2.36 | | 2004/0122516 A1 | 6/2004 | Fogarty et al. ............ 623/2.37 |
| 7,077,862 B2 | 7/2006 | Vidlund et al. ......... 623/2.36 | | 2004/0127979 A1 | 7/2004 | Wilson et al. ............. 623/2.1 |
| 7,081,131 B2 | 7/2006 | Thornton ............... 623/1.24 | | 2004/0127980 A1 | 7/2004 | Kowalsky et al. ......... 623/2.11 |
| 7,087,064 B1 | 8/2006 | Hyde ..................... 606/142 | | 2004/0127981 A1 | 7/2004 | Rahdert et al. ............ 623/2.36 |
| 7,089,051 B2 | 8/2006 | Jäverud et al. ........... 600/547 | | 2004/0127982 A1 | 7/2004 | Machold et al. ........... 623/2.36 |
| 7,090,695 B2 | 8/2006 | Solem et al. ............. 623/2.37 | | 2004/0133220 A1 | 7/2004 | Lashinski et al. ......... 606/151 |
| 2001/0039450 A1 | 11/2001 | Pavcnik et al. ........... 623/1.24 | | 2004/0133267 A1 | 7/2004 | Lane ....................... 623/1.24 |
| 2003/0229394 A1 | 12/2003 | Ogle et al. ................ 623/2.14 | | 2004/0133273 A1 | 7/2004 | Cox ........................ 623/2.11 |
| 2003/0229395 A1 | 12/2003 | Cox ........................ 623/2.36 | | 2004/0138742 A1 | 7/2004 | Myers et al. .............. 623/2.12 |
| 2003/0233142 A1 | 12/2003 | Morales et al. ........... 623/2.37 | | 2004/0138743 A1 | 7/2004 | Myers et al. .............. 623/2.13 |
| 2003/0236568 A1 | 12/2003 | Hojeibane et al. ......... 623/1.24 | | 2004/0138744 A1 | 7/2004 | Lashinski et al. ......... 623/2.36 |
| 2003/0236569 A1 | 12/2003 | Mathis et al. ............. 623/1.26 | | 2004/0138745 A1 | 7/2004 | Macoviak et al. ......... 623/2.36 |
| 2004/0002719 A1 | 1/2004 | Oz et al. .................. 606/142 | | 2004/0148018 A1 | 7/2004 | Carpentier et al. ........ 623/2.18 |
| 2004/0003819 A1 | 1/2004 | St. Goar et al. ............ 128/898 | | 2004/0148019 A1 | 7/2004 | Vidlund et al. ........... 623/2.36 |
| 2004/0010305 A1 | 1/2004 | Alferness et al. .......... 623/1.11 | | 2004/0148020 A1 | 7/2004 | Vidlund et al. ........... 623/2.36 |
| 2004/0015230 A1 | 1/2004 | Moll et al. ................ 623/1.24 | | 2004/0153052 A1 | 8/2004 | Mathis ..................... 606/1 |
| 2004/0015232 A1 | 1/2004 | Shu et al. .................. 623/2.4 | | 2004/0153146 A1 | 8/2004 | Lashinski et al. ......... 623/2.36 |
| 2004/0015233 A1 | 1/2004 | Jansen ..................... 623/2.18 | | 2004/0153147 A1 | 8/2004 | Mathis ..................... 623/2.37 |
| 2004/0019374 A1 | 1/2004 | Hojeibane et al. ......... 623/1.13 | | 2004/0158321 A1 | 8/2004 | Reuter et al. .............. 623/2.36 |
| 2004/0019377 A1 | 1/2004 | Taylor et al. .............. 623/2.11 | | 2004/0162610 A1 | 8/2004 | Liska et al. ............... 623/2.11 |
| 2004/0019378 A1 | 1/2004 | Hlavka et al. ............. 623/2.11 | | 2004/0167539 A1 | 8/2004 | Keuhn et al. .............. 606/108 |
| 2004/0024447 A1 | 2/2004 | Haverich ................... 623/1.24 | | 2004/0167620 A1 | 8/2004 | Ortiz et al. ................ 623/2.11 |
| 2004/0024451 A1 | 2/2004 | Johnson et al. ............ 623/2.11 | | 2004/0172046 A1 | 9/2004 | Hlavka et al. ............. 606/142 |
| 2004/0024452 A1 | 2/2004 | Kruse et al. ............... 623/2.13 | | 2004/0176839 A1 | 9/2004 | Huynh et al. .............. 623/2.4 |
| 2004/0030321 A1 | 2/2004 | Fangrow, Jr. .............. 604/533 | | 2004/0176840 A1 | 9/2004 | Langberg et al. .......... 623/2.37 |
| 2004/0030381 A1 | 2/2004 | Shu ......................... 623/2.11 | | 2004/0181238 A1 | 9/2004 | Zarbatany et al. .......... 606/108 |
| 2004/0030382 A1 | 2/2004 | St. Goar et al. ........... 623/2.36 | | 2004/0186444 A1 | 9/2004 | Daly et al. ................. 604/247 |
| 2004/0030405 A1 | 2/2004 | Carpentier et al. ........ 623/23.72 | | 2004/0186558 A1 | 9/2004 | Pavcnik et al. ............ 623/1.24 |
| 2004/0034380 A1 | 2/2004 | Woolfson et al. .......... 606/170 | | 2004/0186561 A1 | 9/2004 | McGuckin, Jr. et al. .... 623/1.36 |
| 2004/0034411 A1 | 2/2004 | Quijano et al. ............. 623/2.11 | | 2004/0186563 A1 | 9/2004 | Iobbi ....................... 623/2.11 |
| 2004/0039436 A1 | 2/2004 | Spenser et al. ............. 623/1.13 | | 2004/0186565 A1 | 9/2004 | Shreck ..................... 623/2.18 |
| 2004/0039442 A1 | 2/2004 | St. Goar et al. ........... 623/2.36 | | 2004/0186566 A1 | 9/2004 | Hindrichs et al. .......... 623/2.37 |
| 2004/0039443 A1 | 2/2004 | Solem et al. ............... 623/2.37 | | 2004/0193191 A1 | 9/2004 | Starksen et al. ........... 606/153 |
| 2004/0044350 A1 | 3/2004 | Martin et al. .............. 606/139 | | 2004/0193253 A1 | 9/2004 | Thorpe et al. ............. 623/1.24 |
| 2004/0044365 A1 | 3/2004 | Bachman ................... 606/213 | | 2004/0193260 A1 | 9/2004 | Alferness et al. .......... 623/2.11 |
| 2004/0044403 A1 | 3/2004 | Bischoff et al. ............ 623/1.41 | | 2004/0199155 A1 | 10/2004 | Mollenauer ................ 606/27 |
| 2004/0049207 A1 | 3/2004 | Goldfarb et al. ........... 606/139 | | 2004/0199183 A1 | 10/2004 | Oz et al. .................... 606/142 |
| 2004/0049211 A1 | 3/2004 | Tremulis et al. ........... 606/153 | | 2004/0199191 A1 | 10/2004 | Schwartz .................. 606/159 |
| 2004/0049266 A1 | 3/2004 | Anduiza et al. ............ 623/2.11 | | 2004/0204758 A1 | 10/2004 | Eberhardt et al. .......... 623/2.15 |
| 2004/0059351 A1 | 3/2004 | Eigler et al. ............... 606/148 | | 2004/0206363 A1 | 10/2004 | McCarthy et al. .......... 128/898 |
| 2004/0059411 A1 | 3/2004 | Strecker ................... 623/1.23 | | 2004/0210240 A1 | 10/2004 | Saint ........................ 606/139 |
| 2004/0059412 A1 | 3/2004 | Lytle, IV et al. ........... 623/2.11 | | 2004/0210301 A1 | 10/2004 | Obermiller ................. 623/1.24 |
| 2004/0060161 A1 | 4/2004 | Leal et al. .................. 29/558 | | 2004/0210303 A1 | 10/2004 | Sedransk ................... 623/2.1 |
| 2004/0073301 A1 | 4/2004 | Donlon et al. ............. 623/2.11 | | 2004/0210304 A1 | 10/2004 | Seguin et al. .............. 623/2.11 |
| 2004/0073302 A1 | 4/2004 | Rourke et al. ............. 623/2.36 | | 2004/0210305 A1 | 10/2004 | Shu et al. .................. 623/2.11 |
| 2004/0078072 A1 | 4/2004 | Tu et al. ................... 623/1.23 | | 2004/0210306 A1 | 10/2004 | Quijano et al. ............ 623/2.17 |
| 2004/0078074 A1 | 4/2004 | Anderson et al. .......... 623/2.11 | | 2004/0210307 A1 | 10/2004 | Khairkhahan ............. 623/2.18 |
| 2004/0082910 A1 | 4/2004 | Constantz et al. ........ 604/101.04 | | 2004/0215333 A1 | 10/2004 | Duran et al. ............... 623/1.24 |
| 2004/0082923 A1 | 4/2004 | Field ........................ 604/267 | | 2004/0215339 A1 | 10/2004 | Drasler et al. ............. 623/3.1 |
| 2004/0082991 A1 | 4/2004 | Nguyen et al. ............ 623/2.14 | | 2004/0220654 A1 | 11/2004 | Mathis et al. ............. 623/1.11 |
| 2004/0087975 A1 | 5/2004 | Lucatero et al. ........... 606/139 | | 2004/0220657 A1 | 11/2004 | Nieminen et al. ......... 623/1.15 |
| 2004/0088045 A1 | 5/2004 | Cox ........................ 623/2.13 | | 2004/0225322 A1 | 11/2004 | Garrison et al. ........... 606/200 |
| 2004/0088046 A1 | 5/2004 | Speziali ................... 623/2.19 | | 2004/0225344 A1 | 11/2004 | Hoffa et al. ............... 623/1.1 |
| 2004/0092858 A1 | 5/2004 | Wilson et al. ............. 604/9 | | 2004/0225348 A1 | 11/2004 | Case et al. ................. 623/1.15 |
| 2004/0093060 A1 | 5/2004 | Seguin et al. .............. 623/1.11 | | 2004/0225352 A1 | 11/2004 | Osborne et al. ........... 623/1.24 |
| 2004/0093070 A1 | 5/2004 | Hojeibane et al. ......... 623/1.15 | | 2004/0225353 A1 | 11/2004 | McGuckin, Jr. et al. .... 623/2.11 |
| 2004/0093080 A1 | 5/2004 | Helmus et al. ............ 623/2.41 | | 2004/0225354 A1 | 11/2004 | Allen et al. ............... 623/2.11 |
| 2004/0097979 A1 | 5/2004 | Svanidze et al. .......... 606/151 | | 2004/0225355 A1 | 11/2004 | Stevens .................... 623/2.11 |
| 2004/0098098 A1 | 5/2004 | McGuckin, Jr. et al. .... 623/1.14 | | 2004/0225356 A1 | 11/2004 | Frater ...................... 623/2.14 |
| 2004/0098112 A1 | 5/2004 | DiMatteo et al. .......... 623/1.24 | | 2004/0230117 A1 | 11/2004 | Tosaya et al. ............. 600/439 |
| 2004/0102839 A1 | 5/2004 | Cohn et al. ................ 623/2.11 | | 2004/0230297 A1 | 11/2004 | Thornton .................. 623/1.24 |
| 2004/0102840 A1 | 5/2004 | Solem et al. ............... 623/2.11 | | 2004/0236411 A1 | 11/2004 | Sarac et al. ............... 623/1.26 |
| 2004/0102842 A1 | 5/2004 | Jansen ..................... 623/2.38 | | 2004/0236418 A1 | 11/2004 | Stevens .................... 623/2.11 |
| 2004/0106976 A1 | 6/2004 | Bailey et al. .............. 623/1.11 | | 2004/0236419 A1 | 11/2004 | Milo ........................ 623/2.36 |
| 2004/0106990 A1 | 6/2004 | Spence et al. ............. 623/2.11 | | 2004/0243153 A1 | 12/2004 | Liddicoat et al. .......... 606/151 |
| 2004/0106991 A1 | 6/2004 | Hopkins et al. ........... 623/2.13 | | 2004/0243219 A1 | 12/2004 | Fischer et al. ............. 623/1.15 |
| 2004/0111096 A1 | 6/2004 | Tu et al. ................... 606/108 | | 2004/0243227 A1 | 12/2004 | Starksen et al. ........... 623/2.11 |
| 2004/0117009 A1 | 6/2004 | Cali et al. ................. 623/2.12 | | 2004/0243228 A1 | 12/2004 | Kowalsky et al. ......... 623/2.11 |
| 2004/0122448 A1 | 6/2004 | Levine ..................... 606/139 | | 2004/0243230 A1 | 12/2004 | Navia et al. ............... 623/2.36 |
| 2004/0122512 A1 | 6/2004 | Navia et al. ............... 623/2.12 | | 2004/0249452 A1 | 12/2004 | Adams et al. ............. 623/2.36 |
| 2004/0122513 A1 | 6/2004 | Navia et al. ............... 623/2.12 | | 2004/0254600 A1 | 12/2004 | Zarbatany et al. ......... 606/194 |
| 2004/0122514 A1 | 6/2004 | Fogarty et al. ............. 623/2.14 | | 2004/0254636 A1 | 12/2004 | Flagle et al. .............. 623/1.24 |
| 2004/0122515 A1 | 6/2004 | Chu ........................ 623/2.29 | | 2004/0260276 A1 | 12/2004 | Rudko et al. .............. 606/15 |

| Publication No. | Date | Inventor | Class |
|---|---|---|---|
| 2004/0260317 A1 | 12/2004 | Bloom et al. | 606/151 |
| 2004/0260322 A1 | 12/2004 | Rudko et al. | 606/167 |
| 2004/0260389 A1 | 12/2004 | Case et al. | 623/1.24 |
| 2004/0260390 A1 | 12/2004 | Sarac et al. | 623/1.24 |
| 2004/0260393 A1 | 12/2004 | Rahdert et al. | 623/2.36 |
| 2004/0260394 A1 | 12/2004 | Douk et al. | 623/2.36 |
| 2004/0267357 A1 | 12/2004 | Allen et al. | 623/2.11 |
| 2005/0004583 A1 | 1/2005 | Oz et al. | 606/142 |
| 2005/0004667 A1 | 1/2005 | Swinford et al. | 623/2.36 |
| 2005/0010285 A1 | 1/2005 | Lambrecht et al. | 623/2.18 |
| 2005/0010287 A1 | 1/2005 | Macoviak et al. | 623/2.36 |
| 2005/0015112 A1 | 1/2005 | Cohn et al. | 606/200 |
| 2005/0021056 A1 | 1/2005 | St. Goar et al. | 606/144 |
| 2005/0021136 A1 | 1/2005 | Xie et al. | 623/2.14 |
| 2005/0027261 A1 | 2/2005 | Weaver et al. | 604/246 |
| 2005/0027348 A1 | 2/2005 | Case et al. | 623/1.24 |
| 2005/0027351 A1 | 2/2005 | Reuter et al. | 623/2.11 |
| 2005/0027353 A1 | 2/2005 | Alferness et al. | 623/2.11 |
| 2005/0033398 A1 | 2/2005 | Seguin | 623/1.11 |
| 2005/0033419 A1 | 2/2005 | Alferness et al. | 623/2.11 |
| 2005/0033446 A1 | 2/2005 | Deem et al. | 623/23.6 |
| 2005/0038506 A1 | 2/2005 | Webler et al. | 623/2.11 |
| 2005/0038507 A1 | 2/2005 | Alferness et al. | 623/2.11 |
| 2005/0043790 A1 | 2/2005 | Seguin | 623/2.18 |
| 2005/0043792 A1 | 2/2005 | Solem et al. | 623/2.36 |
| 2005/0049679 A1 | 3/2005 | Taylor et al. | 623/1.15 |
| 2005/0049692 A1 | 3/2005 | Numamoto et al. | 623/1.24 |
| 2005/0049696 A1 | 3/2005 | Siess et al. | 623/2.11 |
| 2005/0049697 A1 | 3/2005 | Sievers | 623/2.26 |
| 2005/0054977 A1 | 3/2005 | Laird et al. | 604/96.01 |
| 2005/0055079 A1 | 3/2005 | Duran | 623/1.13 |
| 2005/0055087 A1 | 3/2005 | Starksen | 623/2.11 |
| 2005/0055088 A1 | 3/2005 | Liddicoat et al. | 623/2.11 |
| 2005/0055089 A1 | 3/2005 | Macoviak et al. | 623/2.37 |
| 2005/0060029 A1 | 3/2005 | Le et al. | 623/2.11 |
| 2005/0060030 A1 | 3/2005 | Lashinski et al. | 623/2.37 |
| 2005/0065460 A1 | 3/2005 | Laird | 604/20 |
| 2005/0065550 A1 | 3/2005 | Starksen et al. | 606/219 |
| 2005/0065594 A1 | 3/2005 | Dimatteo et al. | 623/1.24 |
| 2005/0065597 A1 | 3/2005 | Lansac | 623/2.11 |
| 2005/0070998 A1 | 3/2005 | Rourke et al. | 623/2.11 |
| 2005/0075584 A1 | 4/2005 | Cali | 600/587 |
| 2005/0075659 A1 | 4/2005 | Realyvasquez et al. | 606/167 |
| 2005/0075662 A1 | 4/2005 | Pedersen et al. | 606/194 |
| 2005/0075712 A1 | 4/2005 | Biancucci et al. | 623/1.11 |
| 2005/0075713 A1 | 4/2005 | Biancucci et al. | 623/1.11 |
| 2005/0075717 A1 | 4/2005 | Nguyen et al. | 623/1.26 |
| 2005/0075718 A1 | 4/2005 | Nguyen et al. | 623/1.26 |
| 2005/0075719 A1 | 4/2005 | Bergheim | 623/1.26 |
| 2005/0075720 A1 | 4/2005 | Nguyen et al. | 623/1.26 |
| 2005/0075662 A1 | 4/2005 | Schroeder et al. | 623/2.1 |
| 2005/0075723 A1 | 4/2005 | Svanidze et al. | 623/2.11 |
| 2005/0075725 A1 | 4/2005 | Rowe | 623/2.14 |
| 2005/0075726 A1 | 4/2005 | Svanidze et al. | 623/2.14 |
| 2005/0075728 A1 | 4/2005 | Nguyen et al. | 623/2.17 |
| 2005/0075729 A1 | 4/2005 | Nguyen et al. | 623/2.18 |
| 2005/0075730 A1 | 4/2005 | Myers et al. | 623/2.18 |
| 2005/0075731 A1 | 4/2005 | Artof et al. | 623/2.18 |
| 2005/0080483 A1 | 4/2005 | Solem et al. | 623/2.11 |
| 2005/0085900 A1 | 4/2005 | Case et al. | 623/1.24 |
| 2005/0085903 A1 | 4/2005 | Lau | 623/2.11 |
| 2005/0085904 A1 | 4/2005 | Lemmon | 623/2.11 |
| 2005/0090846 A1 | 4/2005 | Pedersen et al. | 606/159 |
| 2005/0096735 A1 | 5/2005 | Hojeibane et al. | 623/1.24 |
| 2005/0096738 A1 | 5/2005 | Cali et al. | 623/2.18 |
| 2005/0096739 A1 | 5/2005 | Cao | 623/2.19 |
| 2005/0096740 A1 | 5/2005 | Langberg et al. | 623/2.36 |
| 2005/0101975 A1 | 5/2005 | Nguyen et al. | 606/151 |
| 2005/0102026 A1 | 5/2005 | Turner et al. | 623/2.1 |
| 2005/0107810 A1 | 5/2005 | Morales et al. | 616/143 |
| 2005/0107811 A1 | 5/2005 | Starksen et al. | 606/143 |
| 2005/0107812 A1 | 5/2005 | Starksen et al. | 606/143 |
| 2005/0107872 A1 | 5/2005 | Mensah et al. | 623/2.14 |
| 2005/0113910 A1 | 5/2005 | Paniagua et al. | 623/2.14 |
| 2005/0119673 A1 | 6/2005 | Gordon et al. | 606/151 |
| 2005/0119734 A1 | 6/2005 | Spence et al. | 623/2.11 |
| 2005/0119735 A1 | 6/2005 | Spence et al. | 623/2.36 |
| 2005/0125011 A1 | 6/2005 | Spence et al. | 606/144 |
| 2005/0131438 A1 | 6/2005 | Cohn | 606/170 |
| 2005/0137449 A1 | 6/2005 | Nieminen et al. | 600/37 |
| 2005/0137450 A1 | 6/2005 | Aronson et al. | 600/37 |
| 2005/0137451 A1 | 6/2005 | Gordon et al. | 600/37 |
| 2005/0137676 A1 | 6/2005 | Richardson et al. | 623/1.11 |
| 2005/0137681 A1 | 6/2005 | Shoemaker et al. | 623/1.23 |
| 2005/0137682 A1 | 6/2005 | Justino | 623/1.24 |
| 2005/0137685 A1 | 6/2005 | Nieminen et al. | 623/2.11 |
| 2005/0137686 A1 | 6/2005 | Salahieh et al. | 623/2.11 |
| 2005/0137688 A1 | 6/2005 | Salahieh et al. | 623/2.11 |
| 2005/0137689 A1 | 6/2005 | Salahieh et al. | 623/2.11 |
| 2005/0137690 A1 | 6/2005 | Salahieh et al. | 623/2.11 |
| 2005/0137691 A1 | 6/2005 | Salahieh et al. | 623/2.11 |
| 2005/0137692 A1 | 6/2005 | Haug et al. | 623/2.11 |
| 2005/0137693 A1 | 6/2005 | Haug et al. | 623/2.11 |
| 2005/0137694 A1 | 6/2005 | Haug et al. | 623/2.11 |
| 2005/0137697 A1 | 6/2005 | Salahieh et al. | 623/2.11 |
| 2005/0137698 A1 | 6/2005 | Salahieh et al. | 623/2.11 |
| 2005/0137699 A1 | 6/2005 | Salahieh et al. | 623/2.11 |
| 2005/0137700 A1 | 6/2005 | Spence et al. | 623/2.36 |
| 2005/0137701 A1 | 6/2005 | Salahieh et al. | 623/2.38 |
| 2005/0137702 A1 | 6/2005 | Haug et al. | 623/2.38 |
| 2005/0137969 A1 | 6/2005 | Salahieh et al. | 623/2.11 |
| 2005/0143807 A1 | 6/2005 | Pavcnik et al. | 623/1.24 |
| 2005/0143809 A1 | 6/2005 | Salahieh et al. | 623/2.11 |
| 2005/0143810 A1 | 6/2005 | Dauner et al. | 623/2.12 |
| 2005/0143811 A1 | 6/2005 | Realyvasquez | 623/2.36 |
| 2005/0149014 A1 | 7/2005 | Hauck et al. | 606/41 |
| 2005/0149179 A1 | 7/2005 | Mathis et al. | 623/2.11 |
| 2005/0149180 A1 | 7/2005 | Mathis et al. | 623/2.11 |
| 2005/0149181 A1 | 7/2005 | Eberhardt | 623/2.14 |
| 2005/0159810 A1 | 7/2005 | Filsoufi | 623/2.1 |
| 2005/0159811 A1 | 7/2005 | Lane | 623/2.14 |
| 2005/0165477 A1 | 7/2005 | Anduiza et al. | 623/2.11 |
| 2005/0165478 A1 | 7/2005 | Song | 623/2.22 |
| 2005/0171472 A1 | 8/2005 | Lutter | 604/101.03 |
| 2005/0171601 A1 | 8/2005 | Cosgrove et al. | 623/2.11 |
| 2005/0177227 A1 | 8/2005 | Heim et al. | 623/2.12 |
| 2005/0177228 A1 | 8/2005 | Solem et al. | 623/2.36 |
| 2005/0182483 A1 | 8/2005 | Osborne et al. | 623/1.24 |
| 2005/0184122 A1 | 8/2005 | Hlavka et al. | 227/175.1 |
| 2005/0187614 A1 | 8/2005 | Agnew | 623/1.24 |
| 2005/0187616 A1 | 8/2005 | Realyvasquez | 623/2.11 |
| 2005/0187617 A1 | 8/2005 | Navia | 623/2.13 |
| 2005/0192606 A1 | 9/2005 | Paul, Jr. et al. | 606/159 |
| 2005/0192665 A1 | 9/2005 | Spenser et al. | 623/2.1 |
| 2005/0197692 A1 | 9/2005 | Pai et al. | 623/2.1 |
| 2005/0197693 A1 | 9/2005 | Pai et al. | 623/2.1 |
| 2005/0197694 A1 | 9/2005 | Pai et al. | 623/2.1 |
| 2005/0203549 A1 | 9/2005 | Realyvasquez | 606/142 |
| 2005/0203605 A1 | 9/2005 | Dolan | 623/1.11 |
| 2005/0203614 A1 | 9/2005 | Forster et al. | 623/2.11 |
| 2005/0203615 A1 | 9/2005 | Forster et al. | 623/2.11 |
| 2005/0203616 A1 | 9/2005 | Cribier | 623/2.11 |
| 2005/0203617 A1 | 9/2005 | Forster et al. | 623/2.14 |
| 2005/0203618 A1 | 9/2005 | Sharkawy et al. | 623/2.38 |
| 2005/0216039 A1 | 9/2005 | Lederman | 606/144 |
| 2005/0216077 A1 | 9/2005 | Mathis et al. | 623/2.11 |
| 2005/0216078 A1 | 9/2005 | Starksen et al. | 623/2.11 |
| 2005/0222675 A1 | 10/2005 | Sauter | 623/1.26 |
| 2005/0222678 A1 | 10/2005 | Lashinski et al. | 623/2.11 |
| 2005/0228422 A1 | 10/2005 | Machold et al. | 606/167 |
| 2005/0228479 A1 | 10/2005 | Pavcnik et al. | 623/1.11 |
| 2005/0228486 A1 | 10/2005 | Case et al. | 623/1.24 |
| 2005/0228494 A1 | 10/2005 | Marquez | 623/2.18 |
| 2005/0228495 A1 | 10/2005 | Macoviak | 623/2.18 |
| 2005/0228496 A1 | 10/2005 | Mensah et al. | 623/2.41 |
| 2005/0234541 A1 | 10/2005 | Hunt et al. | 623/1.24 |

| Publication No. | Date | Inventor | Class |
|---|---|---|---|
| 2005/0234546 A1 | 10/2005 | Nugent et al. | 623/2.11 |
| 2005/0240200 A1 | 10/2005 | Bergheim | 606/108 |
| 2005/0240202 A1 | 10/2005 | Shennib et al. | 606/142 |
| 2005/0240255 A1 | 10/2005 | Schaeffer | 623/1.11 |
| 2005/0240259 A1 | 10/2005 | Sisken et al. | 623/1.36 |
| 2005/0240262 A1 | 10/2005 | White | 623/2.12 |
| 2005/0244460 A1 | 11/2005 | Alferiev et al. | 424/426 |
| 2005/0246013 A1 | 11/2005 | Gabbay | 623/2.1 |
| 2005/0251251 A1 | 11/2005 | Cribier | 623/2.11 |
| 2005/0256566 A1 | 11/2005 | Gabbay | 623/2.1 |
| 2005/0261704 A1 | 11/2005 | Mathis | 606/108 |
| 2005/0261759 A1 | 11/2005 | Lambrecht et al. | 623/1.26 |
| 2005/0267493 A1 | 12/2005 | Schreck et al. | 606/139 |
| 2005/0267560 A1 | 12/2005 | Bates | 623/1.1 |
| 2005/0267565 A1 | 12/2005 | Dave et al. | 623/1.15 |
| 2005/0267571 A1 | 12/2005 | Spence et al. | 623/2.11 |
| 2005/0267573 A9 | 12/2005 | Macoviak et al. | 623/2.36 |
| 2005/0267574 A1 | 12/2005 | Cohn et al. | 623/2.36 |
| 2005/0272969 A1 | 12/2005 | Alferness et al. | 600/37 |
| 2005/0273160 A1 | 12/2005 | Lashinski et al. | 623/1.25 |
| 2005/0278015 A1 | 12/2005 | Dave et al. | 623/1.38 |
| 2005/0283178 A1 | 12/2005 | Flagle et al. | 606/191 |
| 2005/0288779 A1 | 12/2005 | Shaoulian et al. | 623/2.37 |
| 2006/0000715 A1 | 1/2006 | Whitcher et al. | 205/80 |
| 2006/0004439 A1 | 1/2006 | Spenser et al. | 623/1.23 |
| 2006/0004442 A1 | 1/2006 | Spenser et al. | 623/2.11 |
| 2006/0009804 A1 | 1/2006 | Pederson | 607/2 |
| 2006/0009841 A1 | 1/2006 | McGuckin, Jr. et al. | 623/2.38 |
| 2006/0009842 A1 | 1/2006 | Huynh et al. | 623/2.41 |
| 2006/0013805 A1 | 1/2006 | Hebbel et al. | 424/93.21 |
| 2006/0013855 A1 | 1/2006 | Carpenter et al. | 424/423 |
| 2006/0015136 A1 | 1/2006 | Besselink | 606/200 |
| 2006/0015178 A1 | 1/2006 | Moaddeb et al. | 623/2.36 |
| 2006/0015179 A1 | 1/2006 | Bulman-Fleming et al. | 623/2.36 |
| 2006/0020275 A1 | 1/2006 | Goldfarb et al. | 606/151 |
| 2006/0020327 A1 | 1/2006 | Lashinski et al. | 623/1.25 |
| 2006/0020332 A1 | 1/2006 | Lashinski et al. | 623/2.11 |
| 2006/0020334 A1 | 1/2006 | Lashinski et al. | 623/2.11 |
| 2006/0020335 A1 | 1/2006 | Kowalsky et al. | 623/2.36 |
| 2006/0020336 A1 | 1/2006 | Liddicoat | 623/2.37 |
| 2006/0025750 A1 | 2/2006 | Startksen et al. | 604/510 |
| 2006/0025784 A1 | 2/2006 | Startksen et al. | 606/151 |
| 2006/0025787 A1 | 2/2006 | Morales et al. | 606/151 |
| 2006/0025854 A1 | 2/2006 | Lashinski et al. | 623/1.25 |
| 2006/0025855 A1 | 2/2006 | Lashinski et al. | 623/2.1 |
| 2006/0025856 A1 | 2/2006 | Ryan et al. | 623/2.11 |
| 2006/0025857 A1 | 2/2006 | Bergheim et al. | 623/2.18 |
| 2006/0030747 A1 | 2/2006 | Kantrowitz et al. | 600/16 |
| 2006/0030866 A1 | 2/2006 | Schreck | 606/139 |
| 2006/0030882 A1 | 2/2006 | Adams et al. | 606/219 |
| 2006/0030885 A1 | 2/2006 | Hyde | 606/232 |
| 2006/0036317 A1 | 2/2006 | Vidlund et al. | 623/2.36 |
| 2006/0041305 A1 | 2/2006 | Lauterjung | 623/1.36 |
| 2006/0041306 A1 | 2/2006 | Vidlund et al. | 623/2.11 |
| 2006/0047297 A1 | 3/2006 | Case | 606/194 |
| 2006/0047338 A1 | 3/2006 | Jenson | 623/2.11 |
| 2006/0047343 A1 | 3/2006 | Oviatt et al. | 623/915 |
| 2006/0052804 A1 | 3/2006 | Mialhe | 606/157 |
| 2006/0052867 A1 | 3/2006 | Revuelta et al. | 623/2.18 |
| 2006/0058817 A1 | 3/2006 | Starksen et al. | 606/142 |
| 2006/0058865 A1 | 3/2006 | Case et al. | 623/1.11 |
| 2006/0058871 A1 | 3/2006 | Zakay et al. | 623/2.18 |
| 2006/0058889 A1 | 3/2006 | Case et al. | 623/23.68 |
| 2006/0064115 A1 | 3/2006 | Allen et al. | 606/139 |
| 2006/0064116 A1 | 3/2006 | Allen et al. | 606/139 |
| 2006/0064118 A1 | 3/2006 | Kimblad | 606/151 |
| 2006/0064174 A1 | 3/2006 | Zadno | 623/23.68 |
| 2006/0069400 A1 | 3/2006 | Burnett et al. | 606/153 |
| 2006/0069429 A1 | 3/2006 | Spence et al. | 623/2.11 |
| 2006/0069430 A9 | 3/2006 | Rahdert et al. | 623/2.36 |
| 2006/0074483 A1 | 4/2006 | Schrayer | 623/2.1 |
| 2006/0074484 A1 | 4/2006 | Huber | 623/2.11 |
| 2006/0074485 A1 | 4/2006 | Realyvasquez | 623/2.11 |
| 2006/0085060 A1 | 4/2006 | Campbell | 623/1.26 |
| 2006/0089708 A1 | 4/2006 | Osse et al. | 623/1.24 |
| 2006/0095115 A1 | 5/2006 | Bladillah et al. | 623/1.16 |
| 2006/0095125 A1 | 5/2006 | Chinn et al. | 623/2.4 |
| 2006/0099326 A1 | 5/2006 | Keogh et al. | 427/2.36 |
| 2006/0100697 A1 | 5/2006 | Casanova | 623/2.11 |
| 2006/0100699 A1 | 5/2006 | Vidlund et al. | 623/2.36 |
| 2006/0106278 A1 | 5/2006 | Machold et al. | 600/37 |
| 2006/0106279 A1 | 5/2006 | Machold et al. | 600/37 |
| 2006/0106456 A9 | 5/2006 | Machold et al. | 623/2.36 |
| 2006/0111660 A1 | 5/2006 | Wolf et al. | 604/9 |
| 2006/0111773 A1 | 5/2006 | Rittgers et al. | 623/1.24 |
| 2006/0111774 A1 | 5/2006 | Samkov et al. | 623/2.25 |
| 2006/0116572 A1 | 6/2006 | Case | 600/424 |
| 2006/0116756 A1 | 6/2006 | Solem et al. | 623/2.11 |
| 2006/0122686 A1 | 6/2006 | Gilad et al. | 623/1.13 |
| 2006/0122692 A1 | 6/2006 | Gilad et al. | 623/1.24 |
| 2006/0122693 A1 | 6/2006 | Biadillah et al. | 623/1.24 |
| 2006/0127443 A1 | 6/2006 | Helmus | 424/423 |
| 2006/0129235 A1 | 6/2006 | Seguin et al. | 623/2.11 |
| 2006/0129236 A1 | 6/2006 | McCarthy | 623/2.36 |
| 2006/0135476 A1 | 6/2006 | Kutryk et al. | 514/59 |
| 2006/0135964 A1 | 6/2006 | Vesely | 606/108 |
| 2006/0135967 A1 | 6/2006 | Realyvasquez | 606/142 |
| 2006/0136044 A1 | 6/2006 | Osborne | 623/1.24 |
| 2006/0136045 A1 | 6/2006 | Flagle et al. | 623/1.24 |
| 2006/0136052 A1 | 6/2006 | Vesely | 623/2.18 |
| 2006/0136054 A1 | 6/2006 | Berg et al. | 623/2.38 |
| 2006/0142054 A1 | 6/2006 | Pavcnik et al. | 623/1.24 |
| 2006/0142847 A1 | 6/2006 | Shaknovich | 623/1.24 |
| 2006/0142848 A1 | 6/2006 | Gabbay | 623/1.26 |
| 2006/0142854 A1 | 6/2006 | Alferness et al. | 623/2.11 |
| 2006/0149358 A1 | 7/2006 | Zilla et al. | 623/1.22 |
| 2006/0149360 A1 | 7/2006 | Schwammenthal et al. | 623/1.24 |
| 2006/0149367 A1 | 7/2006 | Sieracki | 623/2.21 |
| 2006/0149368 A1 | 7/2006 | Spence | 623/2.37 |
| 2006/0161133 A1 | 7/2006 | Laird et al. | 604/509 |
| 2006/0161248 A1 | 7/2006 | Case et al. | 623/2.1 |
| 2006/0161249 A1 | 7/2006 | Realyvasquez et al. | 623/2.11 |
| 2006/0161250 A1 | 7/2006 | Shaw | 623/2.17 |
| 2006/0167468 A1 | 7/2006 | Gabbay | 606/108 |
| 2006/0167541 A1 | 7/2006 | Lattouf | 623/2.11 |
| 2006/0167542 A1 | 7/2006 | Quintessenza | 623/2.12 |
| 2006/0167543 A1 | 7/2006 | Bailey et al. | 623/2.18 |

FOREIGN PATENT DOCUMENTS

| | | |
|---|---|---|
| WO | WO 02/26168 | 4/2002 |
| WO | WO 2004/019825 | 3/2004 |
| WO | WO 2004/021893 | 3/2004 |
| WO | WO 2004/023980 | 3/2004 |
| WO | WO 2004/030568 | 4/2004 |
| WO | WO 2004/030569 | 4/2004 |
| WO | WO 2004/030570 | 4/2004 |
| WO | WO 2004/032724 | 4/2004 |
| WO | WO 2004/032796 | 4/2004 |
| WO | WO 2004/037128 | 5/2004 |
| WO | WO 2004/037317 | 5/2004 |
| WO | WO 2004/039432 | 5/2004 |
| WO | WO 2004/043265 | 5/2004 |
| WO | WO 2004/043273 | 5/2004 |
| WO | WO 2004/043293 | 5/2004 |
| WO | WO 2004/045370 | 6/2004 |
| WO | WO 2004/045378 | 6/2004 |
| WO | WO 2004/045463 | 6/2004 |
| WO | WO 2004/047677 | 6/2004 |
| WO | WO 2004/060217 | 7/2004 |
| WO | WO 2004/060470 | 7/2004 |
| WO | WO 2004/062725 | 7/2004 |
| WO | WO 2004/066803 | 8/2004 |
| WO | WO 2004/066826 | 8/2004 |
| WO | WO 2004/069287 | 8/2004 |

| | | | | | | |
|---|---|---|---|---|---|---|
| WO | WO2004/075789 | 9/2004 | | WO | WO 2005/055883 | 6/2005 |
| WO | WO2004/080352 | 9/2004 | | WO | WO 2005/058206 | 6/2005 |
| WO | WO2004/082523 | 9/2004 | | WO | WO 2005/065585 | 7/2005 |
| WO | WO2004/082527 | 9/2004 | | WO | WO 2005/065593 | 7/2005 |
| WO | WO2004/082528 | 9/2004 | | WO | WO 2005/065594 | 7/2005 |
| WO | WO2004/082536 | 9/2004 | | WO | WO 2005/070342 | 8/2005 |
| WO | WO2004/082537 | 9/2004 | | WO | WO 2005/070343 | 8/2005 |
| WO | WO2004/082538 | 9/2004 | | WO | WO 2005/072654 | 8/2005 |
| WO | WO2004/082757 | 9/2004 | | WO | WO 2005/072655 | 8/2005 |
| WO | WO 2004/084746 | 10/2004 | | WO | WO 2005/079706 | 9/2005 |
| WO | WO 2004/084770 | 10/2004 | | WO | WO 2005/082288 | 9/2005 |
| WO | WO 2004/089246 | 10/2004 | | WO | WO 2005/082289 | 9/2005 |
| WO | WO 2004/089250 | 10/2004 | | WO | WO 2005/084595 | 9/2005 |
| WO | WO 2004/089253 | 10/2004 | | WO | WO 2005/087139 | 9/2005 |
| WO | WO 2004/091449 | 10/2004 | | WO | WO 2005/087140 | 9/2005 |
| WO | WO 2004/091454 | 10/2004 | | WO | WO 2006/000763 | 1/2006 |
| WO | WO 2004/093638 | 11/2004 | | WO | WO 2006/000776 | 1/2006 |
| WO | WO 2004/093726 | 11/2004 | | WO | WO 2006/002492 | 1/2006 |
| WO | WO 2004/093728 | 11/2004 | | WO | WO 2006/004679 | 1/2006 |
| WO | WO 2004/093730 | 11/2004 | | WO | WO 2006/005015 | 1/2006 |
| WO | WO 2004/093745 | 11/2004 | | WO | WO 2006/009690 | 1/2006 |
| WO | WO 2004/093935 | 11/2004 | | WO | WO 2006/011127 | 2/2006 |
| WO | WO 2004/096100 | 11/2004 | | WO | WO 2006/012011 | 2/2006 |
| WO | WO 2004/103222 | 12/2004 | | WO | WO 2006/012013 | 2/2006 |
| WO | WO 2004/103223 | 12/2004 | | WO | WO 2006/012038 | 2/2006 |
| WO | WO 2004/105584 | 12/2004 | | WO | WO 2006/012068 | 2/2006 |
| WO | WO 2004/105651 | 12/2004 | | WO | WO 2006/012322 | 2/2006 |
| WO | WO 2004/112582 | 12/2004 | | WO | WO 2006/019498 | 2/2006 |
| WO | WO 2004/112585 | 12/2004 | | WO | WO 2006/026371 | 3/2006 |
| WO | WO 2004/112643 | 12/2004 | | WO | WO 2006/026377 | 3/2006 |
| WO | WO 2004/112652 | 12/2004 | | WO | WO 2006/026912 | 3/2006 |
| WO | WO 2004/112657 | 12/2004 | | WO | WO 2006/027499 | 3/2006 |
| WO | WO 2004/112658 | 12/2004 | | WO | WO 2006/028821 | 3/2006 |
| WO | WO 2005/000152 | 1/2005 | | WO | WO 2006/029062 | 3/2006 |
| WO | WO 2005/002424 | 1/2005 | | WO | WO 2006/031436 | 3/2006 |
| WO | WO 2005/002466 | 1/2005 | | WO | WO 2006/031469 | 3/2006 |
| WO | WO 2005/004753 | 1/2005 | | WO | WO 2006/032051 | 3/2006 |
| WO | WO 2005/007017 | 1/2005 | | WO | WO 2006/034245 | 3/2006 |
| WO | WO 2005/007018 | 1/2005 | | WO | WO 2006/035415 | 4/2006 |
| WO | WO 2005/007036 | 1/2005 | | WO | WO 2006/041505 | 4/2006 |
| WO | WO 2005/007037 | 1/2005 | | WO | WO 2006/044679 | 4/2006 |
| WO | WO 2005/009285 | 2/2005 | | WO | WO 2006/048664 | 5/2006 |
| WO | WO 2005/009286 | 2/2005 | | WO | WO 2006/050459 | 5/2006 |
| WO | WO 2005/009505 | 2/2005 | | WO | WO 2006/050460 | 5/2006 |
| WO | WO 2005/009506 | 2/2005 | | WO | WO 2006/054107 | 5/2006 |
| WO | WO 2005/011473 | 2/2005 | | WO | WO 2006/054930 | 5/2006 |
| WO | WO 2005/011534 | 2/2005 | | WO | WO 2006/055982 | 5/2006 |
| WO | WO 2005/011535 | 2/2005 | | WO | WO 2006/060546 | 6/2006 |
| WO | WO 2005/013860 | 2/2005 | | WO | WO 2006/063108 | 6/2006 |
| WO | WO 2005/018507 | 3/2005 | | WO | WO 2006/063181 | 6/2006 |
| WO | WO 2005/021063 | 3/2005 | | WO | WO 2006/063199 | 6/2006 |
| WO | WO 2005/023155 | 3/2005 | | WO | WO 2006/064490 | 6/2006 |
| WO | WO 2005/025644 | 3/2005 | | WO | WO 2006/065212 | 6/2006 |
| WO | WO 2005/027790 | 3/2005 | | WO | WO 2006/065930 | 6/2006 |
| WO | WO 2005/027797 | 3/2005 | | WO | WO 2006/066148 | 6/2006 |
| WO | WO 2005/034812 | 4/2005 | | WO | WO 2006/066150 | 6/2006 |
| WO | WO 2005/039428 | 5/2005 | | WO | WO 2006/069094 | 6/2006 |
| WO | WO 2005/039452 | 5/2005 | | WO | WO 2006/070372 | 7/2006 |
| WO | WO 2005/046488 | 5/2005 | | WO | WO 2006/073628 | 7/2006 |
| WO | WO 2005/046528 | 5/2005 | | WO | WO 2006/076890 | 7/2006 |
| WO | WO 2005/046529 | 5/2005 | | | | |
| WO | WO 2005/046530 | 5/2005 | | | | |
| WO | WO 2005/046531 | 5/2005 | | | | |
| WO | WO 2005/048883 | 6/2005 | | | | |
| WO | WO 2005/049103 | 6/2005 | | | | |
| WO | WO 2005/051226 | 6/2005 | | | | |
| WO | WO 2005/055811 | 6/2005 | | | | |

OTHER PUBLICATIONS

US 6,673,110, 01/2004, Alfieri et al. (withdrawn)
US 6,723,117, 04/2004, Menz et al. (withdrawn)

* cited by examiner

VENOUS VALVE APPARATUS AND METHOD

This application claims priority from U.S. Provisional Application Ser. No. 60/420,905, filed Oct. 24, 2002, the entire content of which is incorporated herein by reference.

TECHNICAL FIELD

The present invention relates generally to apparatus, systems, and methods for use in a body lumen; and more particularly to a valve apparatus for use in the vasculature.

BACKGROUND

In human pathology, the proper functioning of venous valves is important. Chronic venous diseases such as chronic venous insufficiency and varicose veins may result in incompetence of venous valves. Venous insufficiency is believed to contribute to various maladies, including chronic venous insufficiency, edema, varicose veins, aching leg pain while standing, lipodermatosclerosis, and ulcerations. Venous insufficiency is essentially caused by venous hypertension and chronic venous stasis due to valvular incompetence both of an idiopathic nature and of a secondary nature following past illnesses of the venous systems.

A replacement venous valve may regulate the direction of the pulsating blood flow so as to limit the occurrence of blood stasis in the region about the valve. By maintaining the direction of blood flow therethrough a new venous valve may alleviate the maladies resulting from valve disorders or venous insufficiency. A replacement valve should therefore permit blood flow in the proper predetermined direction to limit or prevent backflow of the blood in a reverse direction.

BRIEF DESCRIPTION OF DRAWINGS

A detailed description of the invention is hereafter described with specific reference being made to the drawings.

DETAILED DESCRIPTION

Figure 1:
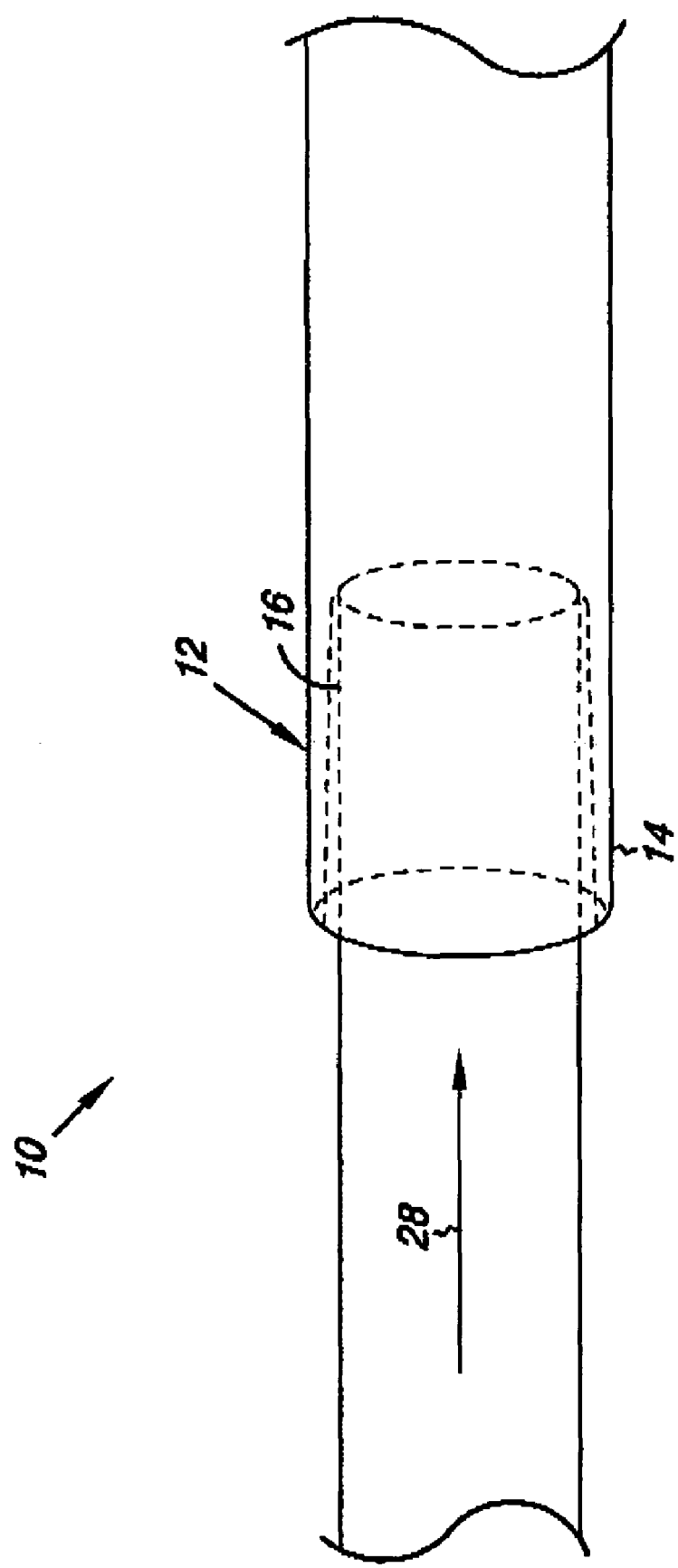
FIG. 1 is a perspective view of an embodiment of the invention wherein a portion of a vein is configured to act as a valve.

Embodiments of the present invention may include different forms. The description herein provides an exemplification of the principles of the invention and is not intended to limit the invention to the particular embodiments illustrated. For the purposes of this disclosure, like reference numerals in the figures shall refer to like features unless otherwise indicated.

The present invention is directed to several embodiments. For example, in at least one embodiment the invention is directed to an apparatus for forming a valve in a vein utilizing the vein itself to form the valve. In some embodiments the apparatus includes a support and/or a fixation device that may be used to form the valve intravenously, extravenously or in a combination of intravenous, and extravenous locations.

In some embodiments the apparatus includes, but is not limited to, one or more ring-like support members or saddles, which retain portions of the vein wall in a position to form a functional valve. In some embodiments the apparatus further includes, but is not limited to, a stent or other implantable and expandable medical device to provide a fold region within the vein through which portions of the vein and support member are positioned to form the valve.

In at least one embodiment the invention is directed to a method of forming a valve utilizing the vein itself. In some embodiments the invention is directed to a method for dissecting the vein from surrounding tissue, thereby freeing the vein to allow longitudinal and axial movement and repositioning of a portion of the vein to form the valve. In some embodiments portions of the reconfigured vein may be tacked together to maintain the valve structure. In some embodiments an expandable member such as a stent is deployed within the vein to provide a point about which an adjacent portion of the vein is folded to provide the valve configuration. In some embodiments one or more saddle members are placed in the reconfigured region of the vein to support the vein and maintain the valve configuration.

In at least one embodiment the invention is directed to a method for forming a valve using entirely percutaneous access methods, or by minimally invasive access methods, or a combination thereof. In some embodiments the invention is directed to a catheter assembly and its methods of use for preparing and/or forming a valve region of a vein by collapsing a region of the vein and/or folding the walls of the vein to provide the vein with a valve configuration. In some embodiments the catheter assembly is provided with one or more balloons to define a valve region and/or deploy a stent and/or a saddle in order to establish and/or maintain the valve configuration of the vein.

Turning to FIG. 1 a first embodiment of the invention is depicted which includes a portion of a vein, indicated generally at reference numeral 10, which is folded over itself to provide the vein with a valve region 12. The valve region 12 acts as a unidirectional blood flow valve in the manner of an existing venous valve. Valve region 12 is provided to the vein 10 by folding a first or outer portion 14 of the vein over a second or inner portion 16 of the vein and retaining the folded configuration by engaging one or more portions of the first portion 14 to adjacent portions of the second portion 16. In at least one embodiment the folding is accomplished endoluminally using a catheter rather than using an external surgical approach.

There are several techniques and devices that may be utilized to form the valve region 12 within the vein as well as to maintain the folded configuration of the valve thereafter. For example, in the embodiment shown in FIG. 1, the vein may be endoluminally or surgically manipulated and folded in the manner shown and described herein. To retain the folded configuration of the valve region 12, the outer portion 14 of the folded vein is engaged to the inner portion 16 of the vein at a plurality of points, such as are indicated by reference numerals 18 and 20 in FIGS. 2 and 3.

In some embodiments valve region 12 may be formed using a vein segment or other autologous or non-autologous biological material and implanted into the desired location to provide valve region 12 in vein 10.

Engagement of selected points of the inner portion 16 and outer portion 14 of the vein has the effect of defining a valve opening 22 with the opposing walls 24 and 26 of the inner portion 16. Depending on the tautness of the region of the vein used to define the opening 22, the opening may also be characterized as a slit. When blood is flowing through the opening or slit 22 in a normal prograde direction, such as when the blood is under positive pressure, as indicated by arrow 28 in FIG. 1, the walls 24 and 26 of the inner portion 16 are pushed outward, as indicated by arrows 30 in FIG. 2, to allow free flow of blood through the opening 22. However, if for whatever reason, the flow of blood through the vein is reversed or becomes retrograde, i.e., under negative pressure, the pressure exerted on the opening 22 will cause the walls 24 and 26 to collapse inward, as indicated by arrows 32 in FIG. 3, thus closing the opening 22 and preventing the retrograde flow.

Vein portions 14 and 16 may be engaged together to maintain the valve region 12 in a variety of different and/or complimentary manners. For example, in the embodiment shown in FIGS. 2 and 3 the portions may be sutured, tacked, thermally bonded, glued, and/or otherwise secured together at junctions 18 and 20 or at other areas as may be desired to maintain the valve region 12 and provide the unidirectional opening 22.

In some embodiments a biasing member or support device may be inserted within the vein to maintain the folded configuration of the valve region 12 by pushing selected portions of the inner portion 16 against the outer portion 14 to form opening 22. Some examples of such a support device are shown in FIGS. 4 and 5, wherein a valve maintaining support includes, but is not limited to, a substantially ring-like member or saddle 40, which may inserted into the vein to maintain the folded configuration of the valve region 12 by biasing portions of the inner portion 16 of the vein 10 against corresponding portions of the outer portion 14 of the vein 10 such as in the manner shown in FIG. 6.

Figure 4:
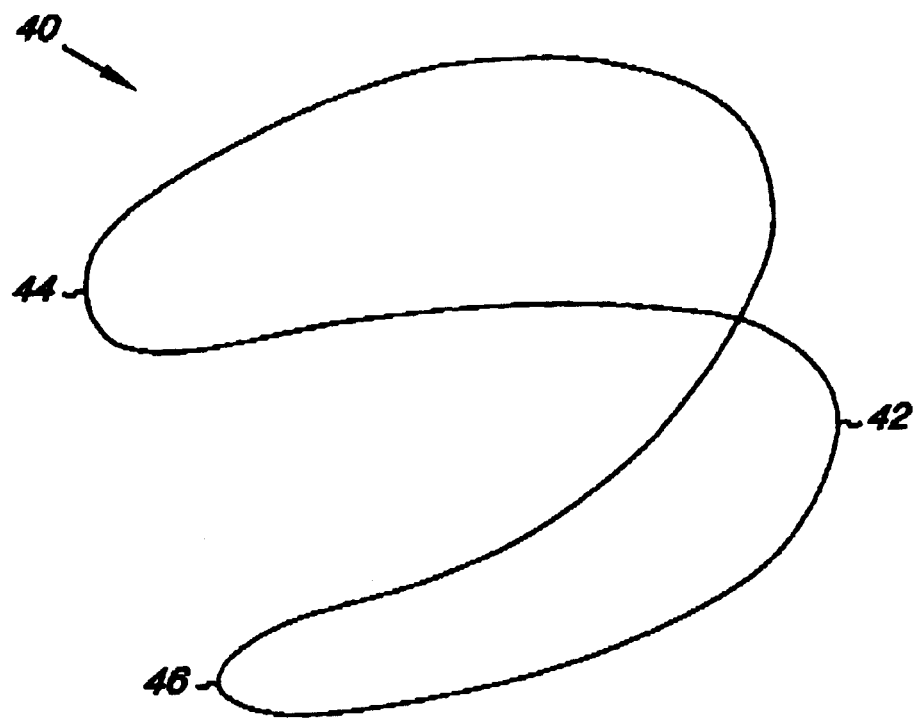
FIG. 4 is a perspective view of an embodiment of the invention including a saddle for establishing and supporting a region of a vein configured to act as a valve.
Figure 5:
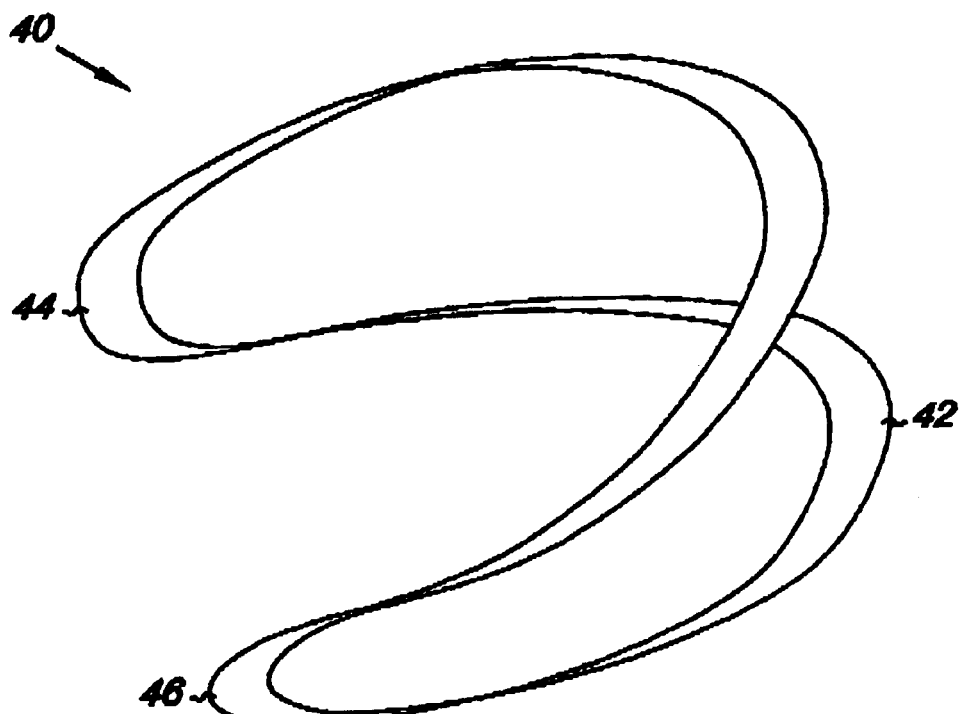
FIG. 5 is a perspective view of an embodiment of the invention including a saddle for establishing and supporting a region of a vein configured to act as a valve.

As shown in FIGS. 4 and 5, the saddle 40 may be constructed of one or more wires or bands 42 of material. The saddle may be constructed from one or more metals and/or polymer materials, including shape memory metals such as nitinol, and/or shape memory polymers, and/or bioabsorbable materials. In one embodiment, the material of the saddle can be biocompatible or is coated with one or more biocompatible coatings.

Figure 6:
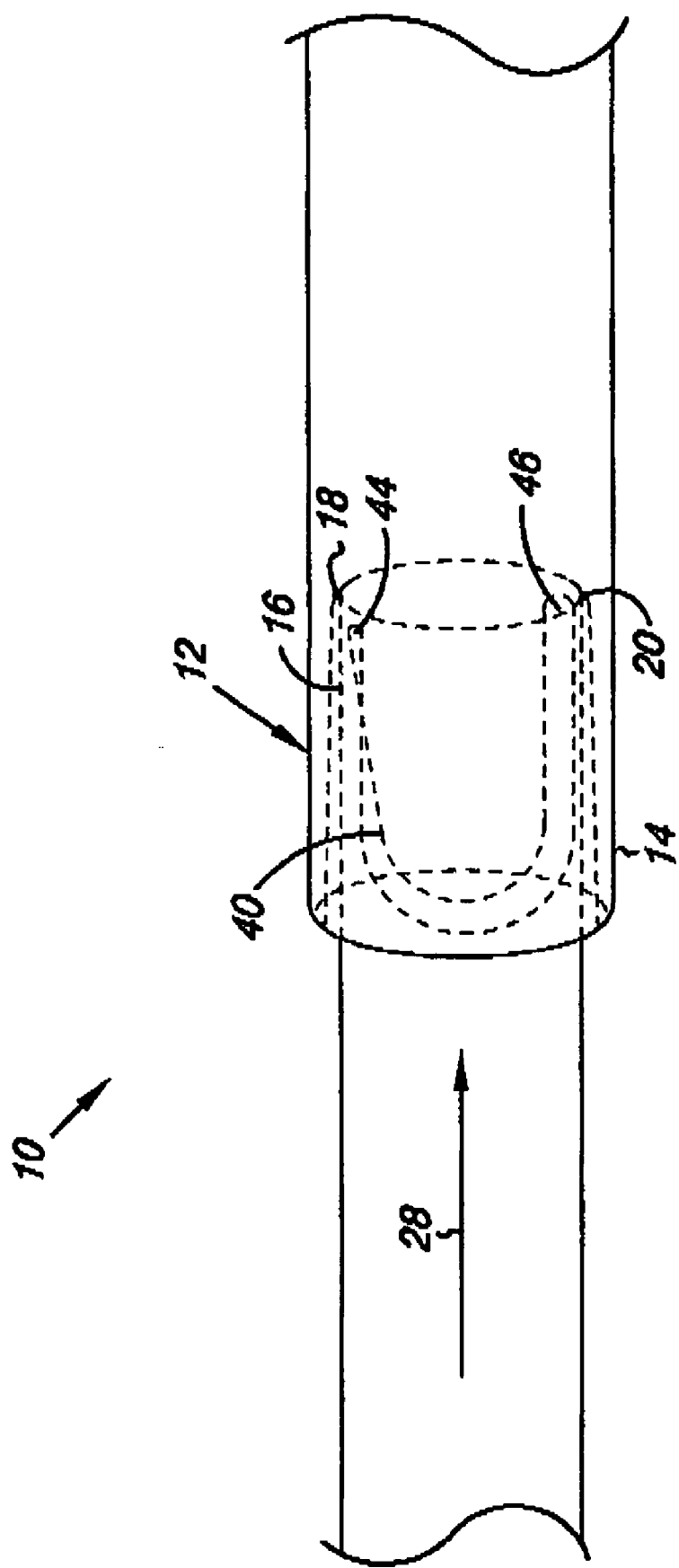
FIG. 6 is a perspective view of the portion of a vein configuration shown in FIG. 1 with the ring support of FIG. 4 positioned therein.

The saddle 40 defines at least two biasing regions 44 and 46 that as a result of inherent biasing tension and/or as a result of transitioning from a reduced state to an expanded shape memory state, push the inner portion 16 of the vein 10 against the outer portion 14 of the vein 10 at junctions 18 and 20 as shown in FIG. 6. As a result, the saddle 40 maintains the folded configuration of the valve region 12 of the vein 10 without the need to surgically or externally affect the vein 10 such as by bonding the vein portions together as previously described, although such procedures may be utilized in conjunction with the saddle 40 if desired.

Some embodiments of the invention may include one or more support devices. For those embodiments having two or more support devices, both devices may be positioned inside the vein, both may be positioned outside the vein, and/or one may be inside and the other outside. Other configurations for the one or more support devices are also possible. Support devices may include one or more saddle-shaped rings, one or more stents or similar structures, and/or a combination of the two. Other types of supports may include an anchor bar extending between opposite sides of the vessel, circular or helical rings, tacks, barbs and interlocking components.

As indicated above, the present invention provides for a variety of methods for forming the folded configuration of the valve region 12, a variety of methods for preparing a selected region of the vein for folding, and a variety of methods for maintaining the valve region 12 in its folded configuration. Additionally, the present invention provides for embodiments directed to catheters and catheter systems for carrying out one or more of the various methods described.

An example of such an inventive catheter assembly, indicated generally at 100, is depicted in FIGS. 7-13. In FIGS. 7-13 the catheter 100 is shown carrying out the steps of at least one of the inventive methods for preparing the vein 10 for folding and folding a portion of the vein 10 to form the valve region and deploying a saddle 40 therein.

Figure 7:
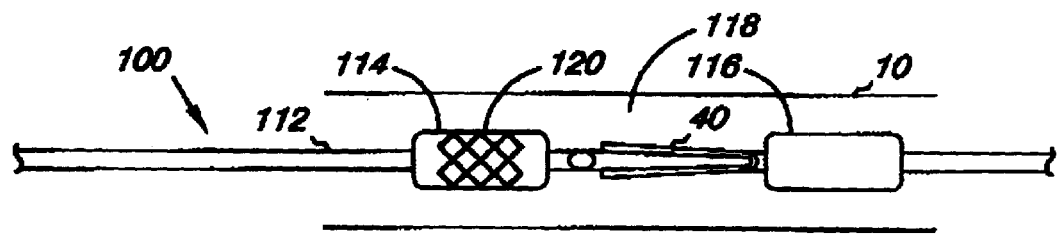
FIG. 7 is a side view of a vein having an embodiment of the invention including a catheter assembly for use in configuring a region of the vein to act as a valve positioned therein.

As is shown in FIG. 7, prior to formation of the valve region the catheter 100 includes, but is not limited to, a catheter shaft 112 having at least two expandable members or balloons 114 and 116 positioned thereon. It should be recognized that it is inherent that the catheter shaft 112 defines an inflation lumen or other mechanism (not shown) for expanding the balloons 114 and 116.

Figure 11:
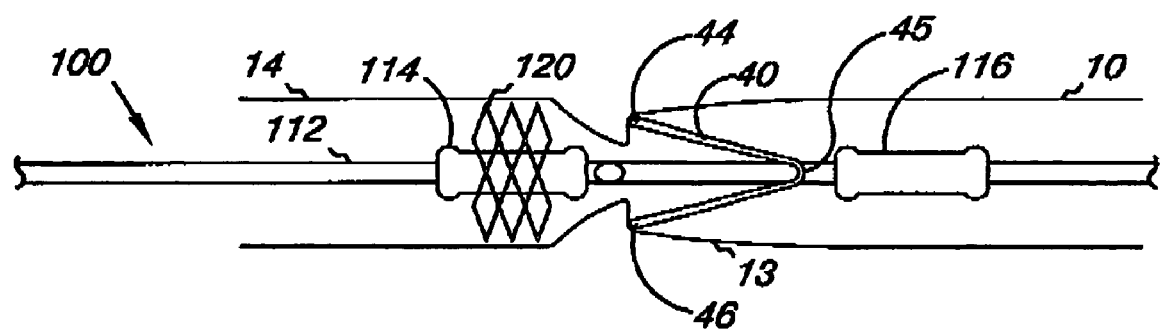
FIG. 11 is a side view of the vein containing the embodiment of the invention depicted in FIG. 10 wherein the saddle is engaged to a portion of the collapsed region of the vein.
Figure 12:
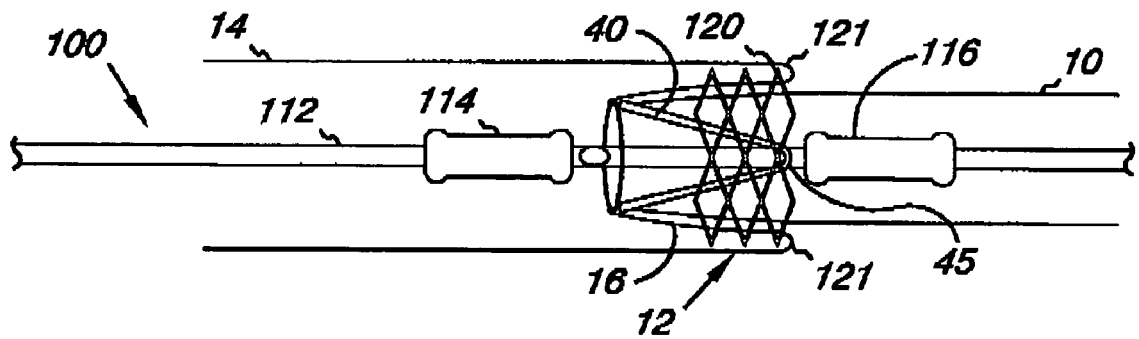
FIG. 12 is a side view of the vein containing the embodiment of the invention wherein the saddle and a portion of the collapsed region of the vein engaged thereto are moved into an adjacent portion of the vein to provide the vein with a valve configuration.
Figure 13:
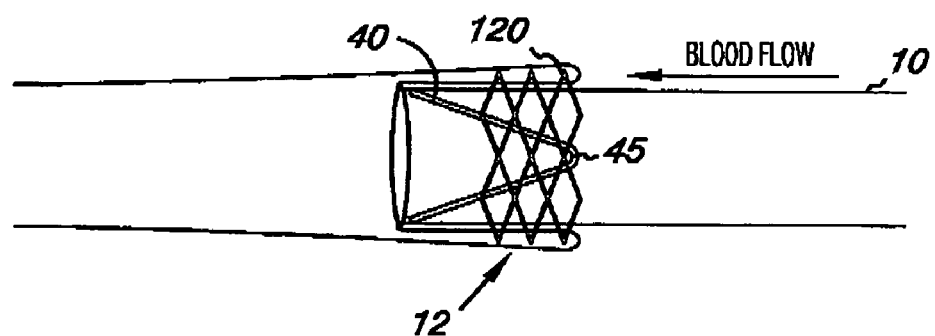
FIG. 13 is side view of the vein shown in FIGS. 7-13 wherein the catheter has been removed from the valve configured region of the vein.

Also disposed about the shaft 112 is a support device or saddle 40 in a reduced low profile configuration. The saddle 40 may be held in the reduced state by any of a variety of known retaining devices such as one or more retractable sleeves, sheaths, socks, and bioabsorbable retaining bands, which when removed from the saddle 40, the saddle is allowed to expand to its nominal or expanded state such as is shown in FIGS. 11-13. In embodiments where the saddle 40 is at least partially constructed of a shape memory material, the saddle may be retained in the reduced profile configuration shown in FIG. 7 until the material is triggered to achieve one or more expanded states such as are shown in FIGS. 11-13.

In some embodiments of the invention the catheter 100 may also be equipped with one or more stents or other expandable endoprosthetic support devices. In the embodiment shown in FIG. 7 the support device can be a stent 120, such as a balloon expandable stent positioned about the first balloon 114. In some embodiments support device may be self-expandable or hybrid expandable as desired and may be positioned anywhere along the catheter shaft 112 prior to delivery.

Figure 8:
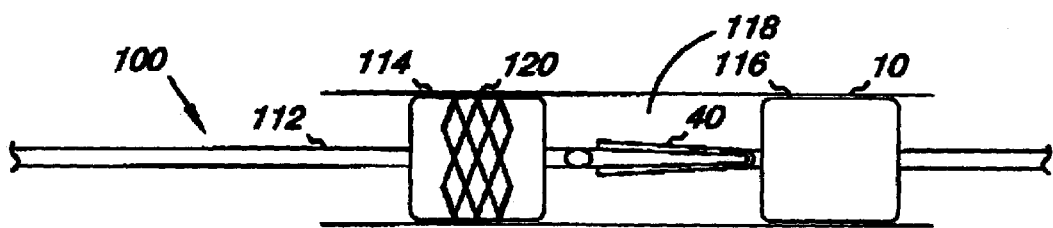
FIG. 8 is a side view of the vein containing the embodiment of the invention depicted in FIG. 7 shown during balloon deployment.

In practice the catheter 100 is advanced through the vein 10 to a selected region 118 of the vein 10 where it is desired to form a valve region. The catheter 100 is positioned such that the balloons 114 and 116 are adjacent to the ends of the selected region 118. Once the catheter 100 is positioned in this manner, the balloons 114 and 116 are expanded such as is shown in FIG. 8 to isolate the region of the vein 10 which is to be prepared for valve formation.

Figure 9:
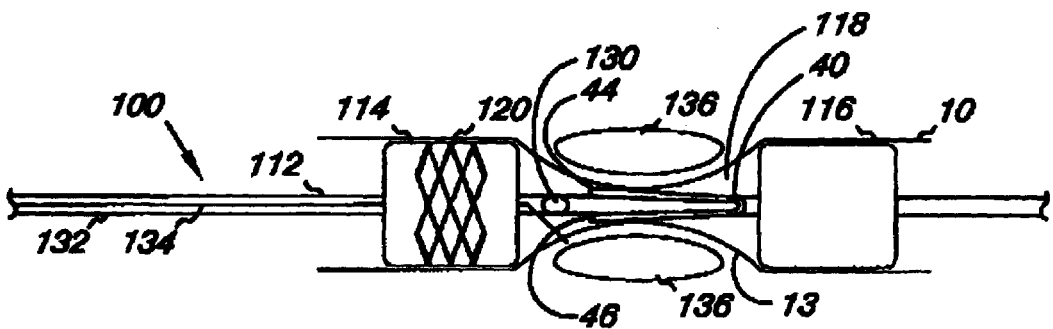
FIG. 9 is a side view of the vein containing the embodiment of the invention depicted in FIG. 8 shown during evacuation of a region of the vein between the deployed balloons to collapse the region.

To facilitate folding the vein 10, it is desirable to collapse the vein 10 in order to facilitate engagement of the vein wall 13 to the biasing regions 44 and 46 of the saddle 40. In some embodiments of the invention the shaft 112 defines a vacuum or evacuation port 130 and an evacuation lumen 132 through which the blood present in the selected region 118 may be evacuated in order to collapse the selected region 118 of the vein 10 as is shown in FIG. 9. In some embodiments of the invention the catheter 100 includes an injection device 134 which is advanced through the shaft 112 and passed outward through the vein wall 13 to deploy inject material 136 about the selected region 118 of the vein 10. The inject material 136 may be any material such as including but not limited to: saline, contrast medium, anesthetic solution, air, carbon dioxide, or any suitable liquid, gas or combination thereof. The inject material 136 will aid in separating the vein 10 from the surrounding extra-vascular tissue and thereby aid in collapsing the isolated selected region 118 with out the need to surgically expose the vein 10.

In some embodiments a device such as a helical wire or other device may be passed around the vein 10 to limit any expansion of the vein 10 which may occur, for example, by internal device expansion such as support device, or by dilatation due to internal pressure. The helical wire or other device can be introduced from within the vein and passed through an opening created in the vein wall, or can be placed surgically.

Figure 10:
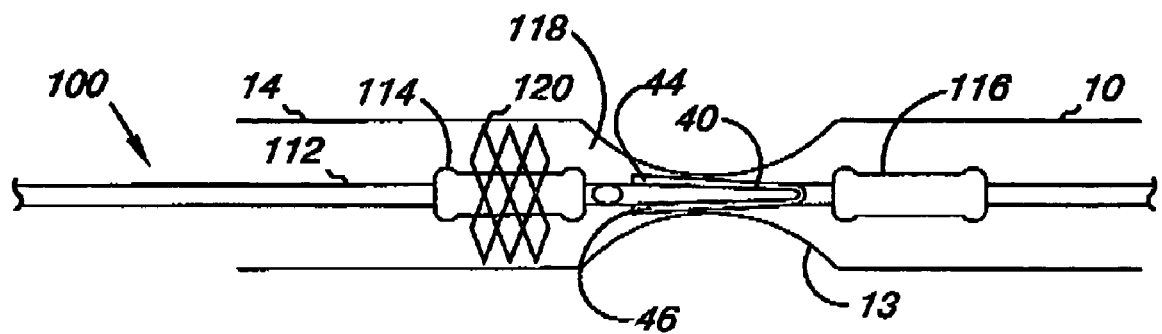
FIG. 10 is a side view of the vein containing the embodiment of the invention depicted in FIG. 9 shown during balloon collapse.

Once the selected region 118 of the vein 10 is collapsed, such as is shown in FIG. 10, the balloons 114 and 116 are collapsed and the stent 120 is deployed adjacent to the collapsed selected region 118 of the vein.

The deployed stent 120 acts to support and define the outer portion 14 of the vein 10. Once the stent 120 is deployed the biasing regions 44 and 46 are freed to expand radially outward from the catheter shaft 112 to engage the wall 13 of the selected region 118 of the vein 10, such as is shown in FIG. 11. When the biasing regions 44 and 46 of the saddle 40 are initially freed to expand the opposing end(s) 45 of the saddle 40 remain in the reduced configuration engaged to the catheter shaft 112.

As is shown in FIG. 12, following the partial deployment of the saddle 40 and engagement of the vein wall 13 by the biasing regions 44 and 46, the catheter 100 is drawn back through the deployed stent 120. Drawing the catheter 100 through the stent 120 pulls the saddle 40 as well as the portion of the vein engaged thereto through the stent 120 as well. Because the stent 120 is fixed in place within the vein 10, the vein wall 13 is forced to fold at fold point 121 about the edge of the stent 120. Thus, the portion of the vein disposed about the stent becomes the outer portion 14 of the valve region 12 and the portion of the vein 10 drawn through the stent 120 becomes the inner portion 16.

Figure 2:
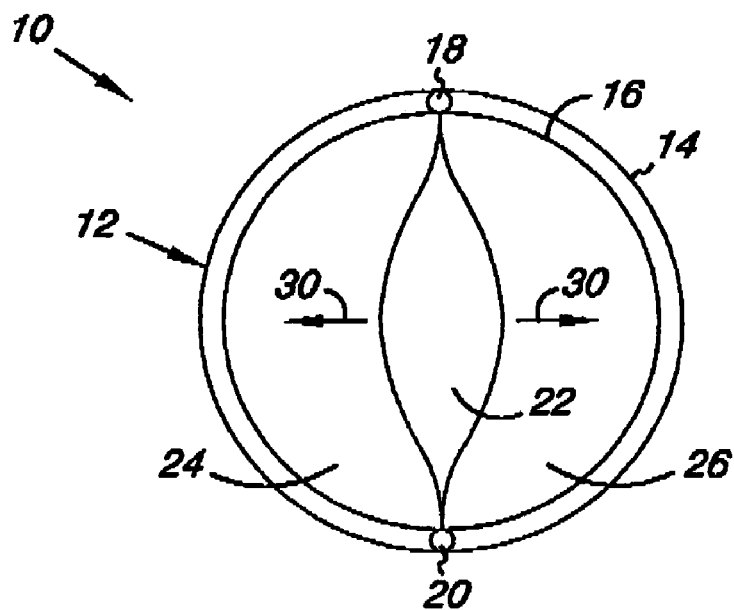
FIG. 2 is a cross-sectional view of the embodiment shown in FIG. 1 wherein the configured vein is shown during prograde blood flow.
Figure 3:
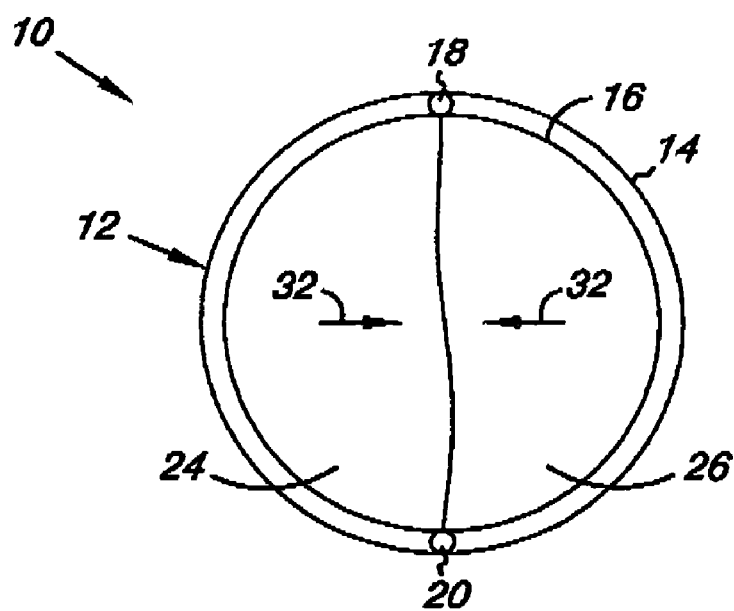
FIG. 3 is a cross-sectional view of the embodiment shown in FIG. 1 wherein the configured vein is shown during retrograde blood flow.

After the valve region 12 is formed in the manner described above, the ends 45 of the saddle 40 are released from the shaft 112 (shown in FIG. 12) and the saddle is allowed to fully deploy within the vein 10 and the catheter may be withdrawn as shown in FIG. 13. The saddle 40 retains the folded configuration of the valve region 12 in the manner previously described to provide the vein 10 with a unidirectional valve such as is shown in FIGS. 2 and 3.

Figure 14:
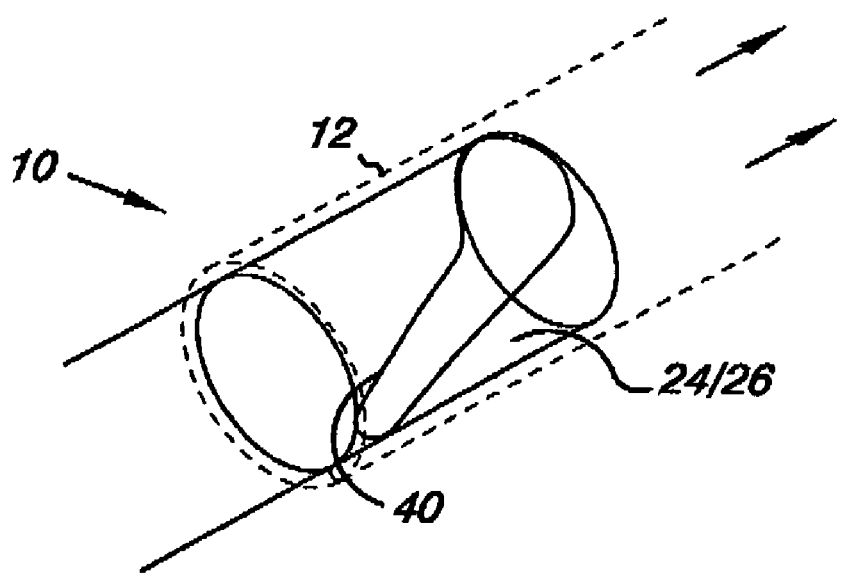
FIG. 14 is a perspective view of an embodiment of the invention wherein the valve region comprises a single valve wall or leaflet.
Figure 15:
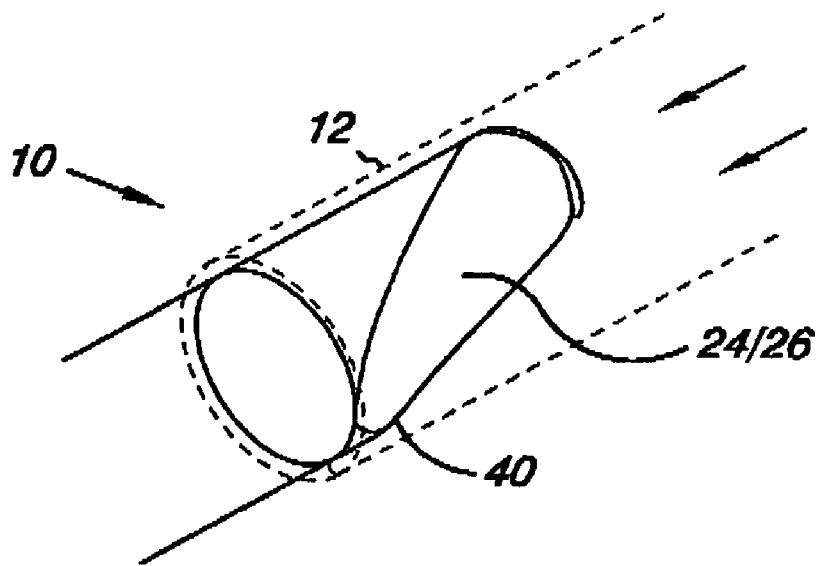
FIG. 15 is a perspective view of the embodiment shown in FIG. 14, with the valve wall or leaflet in the closed configuration.
Figure 16:
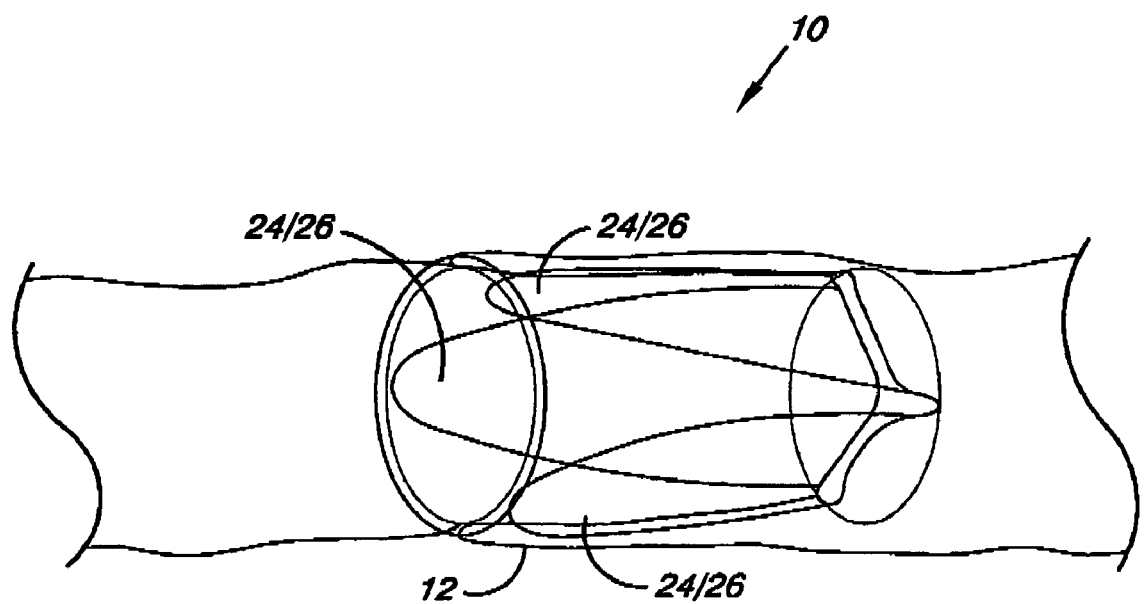
FIG. 16 is a perspective view of an embodiment of the invention wherein the valve region comprises a single valve wall or leaflet.

Although the embodiments depicted in FIGS. 1-13 incorporate valve configurations with two valve leaflet surfaces, the present invention can also be directed to embodiments having one or more leaflets or walls 24/26 such as are depicted in FIGS. 14-16. So, valve configurations can include one, two, or three leaflets analogous to opposing walls 24 and 26 shown in FIGS. 2 and 3.

In FIGS. 14-15 a valve region 12 is provided with a single leaflet or wall 24/26. FIG. 14 shows the vein with the leaflet 24/26 in the open configuration and FIG. 15 shows the leaflet 24/26 in the closed configuration.

In the embodiment shown in FIG. 16, a valve region 12 is shown having three leaflets or walls 24/26.

The above disclosure is intended to be illustrative and not exhaustive. This description will suggest many variations and alternatives to one of ordinary skill in this art. All these alternatives and variations are intended to be included within the scope of the claims. Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the embodiments of the present invention. Those skilled in the art may recognize other equivalents to the specific embodiment described herein which equivalents are intended to be encompassed by the claims attached hereto.

We claim:

1. A catheter for use in forming a unidirectional valve in a vein, the catheter comprising:
   a catheter shaft;
   at least two expandable balloons positioned on the catheter shaft;
   an expandable support member, the expandable support member being disposed about one of the balloons in a reduced state, the expandable support member being expandable from the reduced state to an expanded state; and an expandable saddle member, the expandable saddle member including a first biasing region, a second biasing region and at least one end region, the expandable saddle member having a reduced state, a partially expanded state and a fully expanded state, where in the reduced state for the expandable saddle member the first biasing region, the second biasing region and at least one end region are engaged to the catheter shaft, in the partially expanded state the first biasing region and the second biasing region are free to expand radially outward from the catheter shaft but the at least one end region remains engaged to the catheter shaft, and in the fully expanded state the first biasing region, the second biasing region and the at least one end region are all free to expand radially outward from the catheter shaft.

2. The catheter of claim 1, wherein the catheter shaft defines an evacuation port and an evacuation lumen in fluid communication therewith, the evacuation port being positioned between the at least two expandable balloons.

3. The catheter of claim 1, wherein the catheter further includes an injection device extending along the catheter shaft and is constructed and arranged to be advance through a vein wall to deposit injection material about a selected portion of the vein.

4. The catheter of claim 3, wherein the injection material is selected from at least one member of the group consisting of: saline, contrast medium, anesthetic solution, air, carbon dioxide, and any combination thereof.

5. The catheter of claim 1, wherein the expanded support member includes a stent.

6. The catheter of claim 1, further including a helical member disposed within a lumen of the catheter shaft, wherein the helical member deploys from the lumen and limits the expansion of the expandable support member.

* * * * *